United States Patent [19]

Harris et al.

[11] Patent Number: 5,314,496
[45] Date of Patent: May 24, 1994

[54] STUMP SOCK ARRANGEMENT

[76] Inventors: Bertram H. Harris; Lois E. Harris, both of 224 Valley La., Crossville, Tenn. 38555

[21] Appl. No.: 999,265

[22] Filed: Dec. 31, 1992

[51] Int. Cl.$^5$ .......................... A61F 2/60; A61F 2/68
[52] U.S. Cl. ...................................... 623/31; 602/61; 623/36; 604/306; 604/289; 2/22
[58] Field of Search ............... 602/61, 62, 63, 64, 602/65, 66, 13, 3; 623/27, 31, 32, 36, 37, 34, 33; 604/289, 306, 308; 2/22, 239; 36/2 R

[56] References Cited

U.S. PATENT DOCUMENTS

| | | | |
|---|---|---|---|
| 1,117,725 | 11/1914 | Tullis | 623/37 |
| 2,408,073 | 9/1946 | Kickland | 623/31 |
| 2,483,136 | 9/1949 | Hamman et al. | 36/2 R |
| 2,582,648 | 1/1952 | Mowbray | 2/239 |
| 3,138,156 | 6/1964 | Crowell et al. | 602/61 |
| 3,600,717 | 8/1971 | McKeehan | 623/36 |
| 4,110,845 | 9/1978 | Chellis | 36/2 R |
| 4,840,635 | 6/1989 | Smith et al. | 623/36 |
| 4,917,676 | 4/1990 | Heiber et al. | 604/306 |
| 5,108,455 | 4/1992 | Telikicherla | 623/36 |

*Primary Examiner*—Paul Prebilic
*Attorney, Agent, or Firm*—Gilden Leon

[57] ABSTRACT

A flexible stump sock member is arranged to receive an amputated leg portion therewithin for cushioning the leg portion when positioned within an artificial limb cavity.

2 Claims, 4 Drawing Sheets

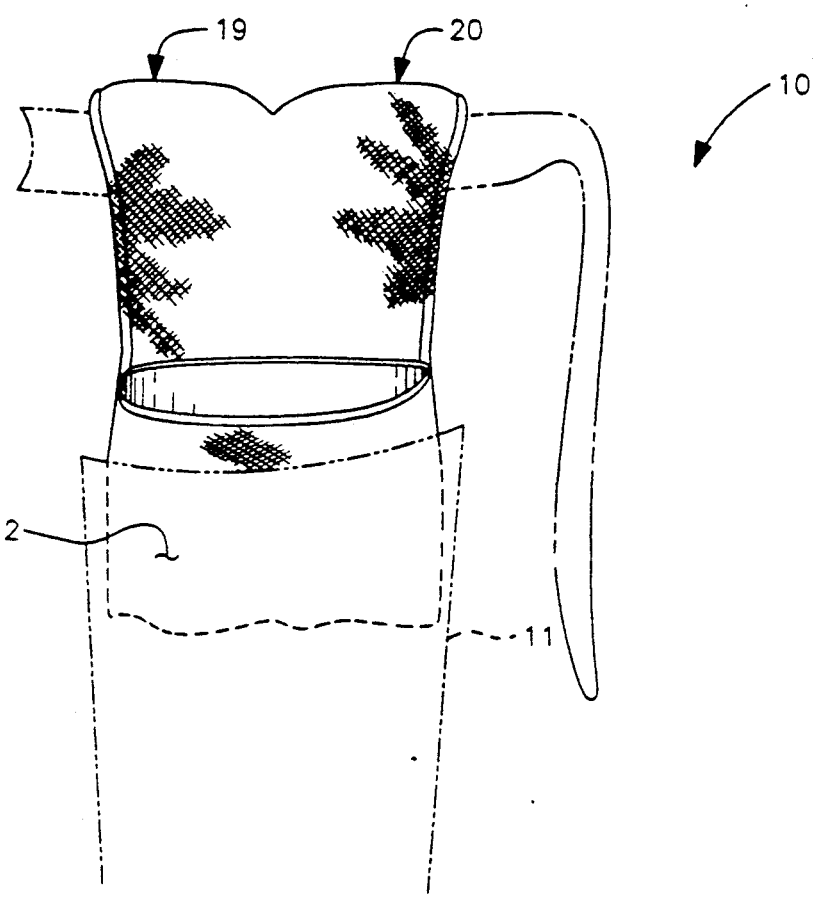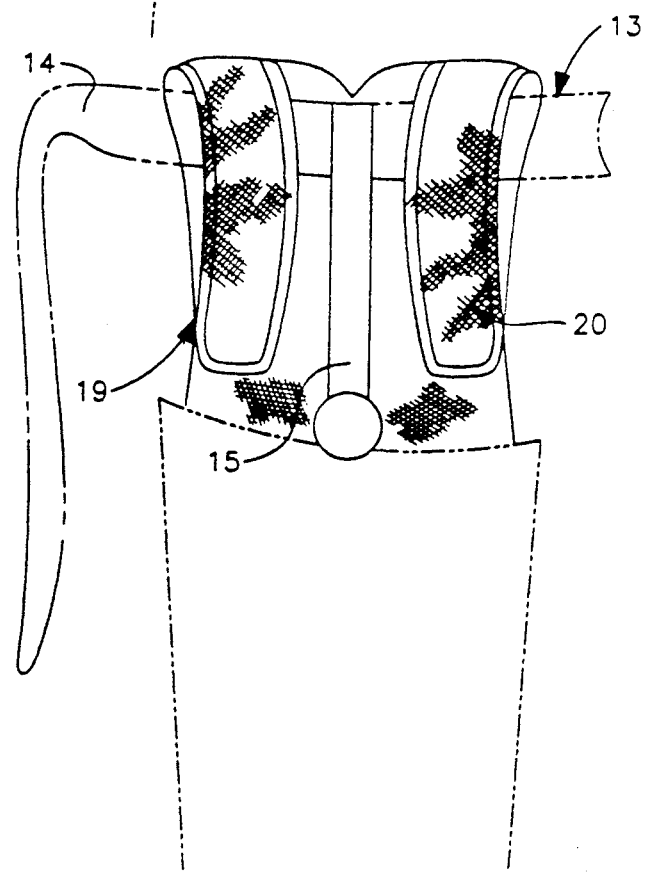

1

STUMP SOCK ARRANGEMENT

BACKGROUND OF THE INVENTION

1. Field of the Invention

The field of invention relates to stump sock structure, and more particularly pertains to a new and improved stump sock arrangement wherein the same is arranged for affording cushioning and protection to an individual's leg portion directed within an artificial leg assembly.

2. Description of the Prior Art

Stump socks of various types have been utilized in the prior art and exemplified by U.S. Pat. Nos. 3,600,717 and 4,840,635.

The instant invention addresses deficiencies of the prior art by providing means for securely mounting the stump sock arrangement relative to an amputated limb of an individual and securing same by means of a support strap structure.

SUMMARY OF THE INVENTION

In view of the foregoing disadvantages inherent in the known types of stump sock structure now present in the prior art, the present invention provides a stump sock arrangement employing a support strap structure mounting the stump sock relative to the strap structure. As such, the general purpose of the present invention, which will be described subsequently in greater detail, is to provide a new and improved stump sock arrangement which has all the advantages of the prior art stump sock structure and none of the disadvantages.

To attain this, the present invention provides a flexible stump sock member arranged to receive an amputated leg portion therewithin for cushioning the leg portion when positioned within an artificial limb cavity.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved stump sock arrangement which has all the advantages of the prior art stump sock structure and none of the disadvantages.

It is another object of the present invention to provide a new and improved stump sock arrangement which may be easily and efficiently manufactured and marketed.

It is a further object of the present invention to provide a new and improved stump sock arrangement which is of a durable and reliable construction.

An even further object of the present invention is to provide a new and improved stump sock arrangement which is susceptible of a low cost of manufacture with regard to both materials and labor, and which accordingly is then susceptible of low prices of sale to the consuming public, thereby making such stump sock arrangements economically available to the buying public.

Still yet another object of the present invention is to provide a new and improved stump sock arrangement which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an orthographic view of the invention arranged for positioning within an associated artificial limb.

FIG. 2 is an orthographic rear view of the invention, as indicated in FIG. 1.

DESCRIPTION OF THE PREFERRED EMBODIMENT

Figure 3:
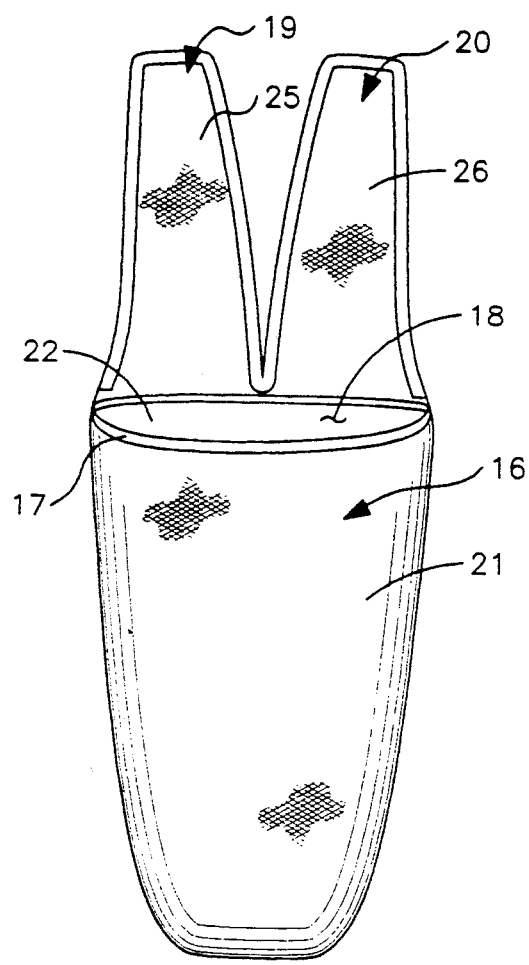
FIG. 3 is an isometric illustration of the sock structure.
Figure 4:
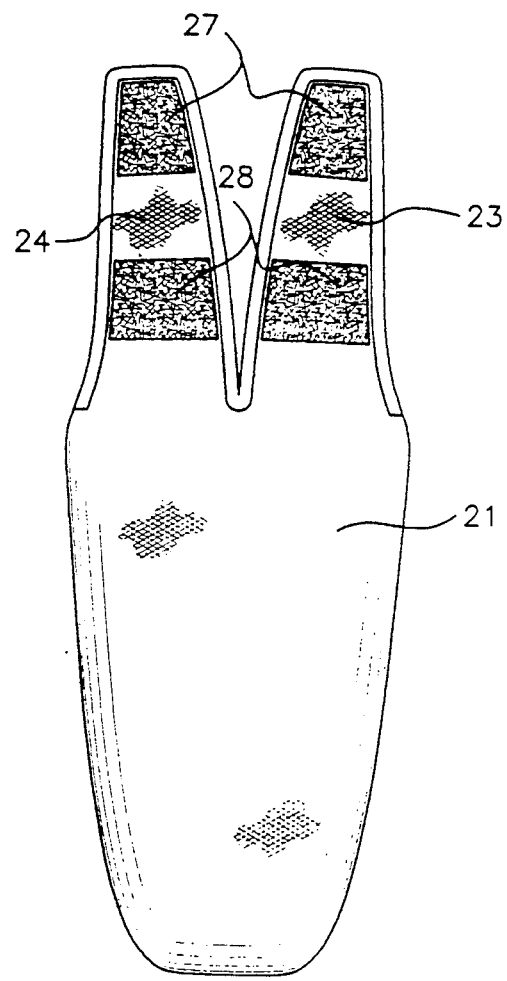
FIG. 4 is an orthographic rear view of the sock structure.

With reference now to the drawings, and in particular to FIGS. 1 to 8 thereof, a new and improved stump sock arrangement embodying the principles and concepts of the present invention and generally designated by the reference numeral 10 will be described.

More specifically, the stump sock arrangement 10 of the instant invention essentially comprises cooperation with an artificial limb 11, as indicated in FIG. 1, having a limb cavity 12 directed therein. A support strap 13 is provided having a thigh strap portion 14 mounted orthogonally relative to an anchor strap 15, that in turn is secured to the artificial limb in adjacency to an entrance of the artificial limb cavity 12. The flexible sock structure includes a flexible sock body 16 having a sock body entrance periphery 17 at an upper end portion of a sock body cavity 18. Respective first and second straps 19 and 20 are provided, each having a predetermined length and mounted in adjacency and in a coextensive relationship relative to one another fixedly secured to the periphery 17. The sock body 16 includes an exterior surface 21, with an interior surface 22. The first and second straps 19 and 20 include respective first and second strap outer surfaces 23 and 24 that are directed to the sock exterior surface 21, with the sock interior surface 22 directed to the first and second straps inner surfaces 25 and 26. The strap inner surfaces include respective first hook and loop fastener patches 27 mounted in a spaced relationship relative to a second hook and loop fastener patch 28, with the first and second hook and loop fastener patches arranged for securement relative to one another of each respective strap for securement about the thigh strap 14, in a manner as indicated in FIG. 2.

Figure 5:
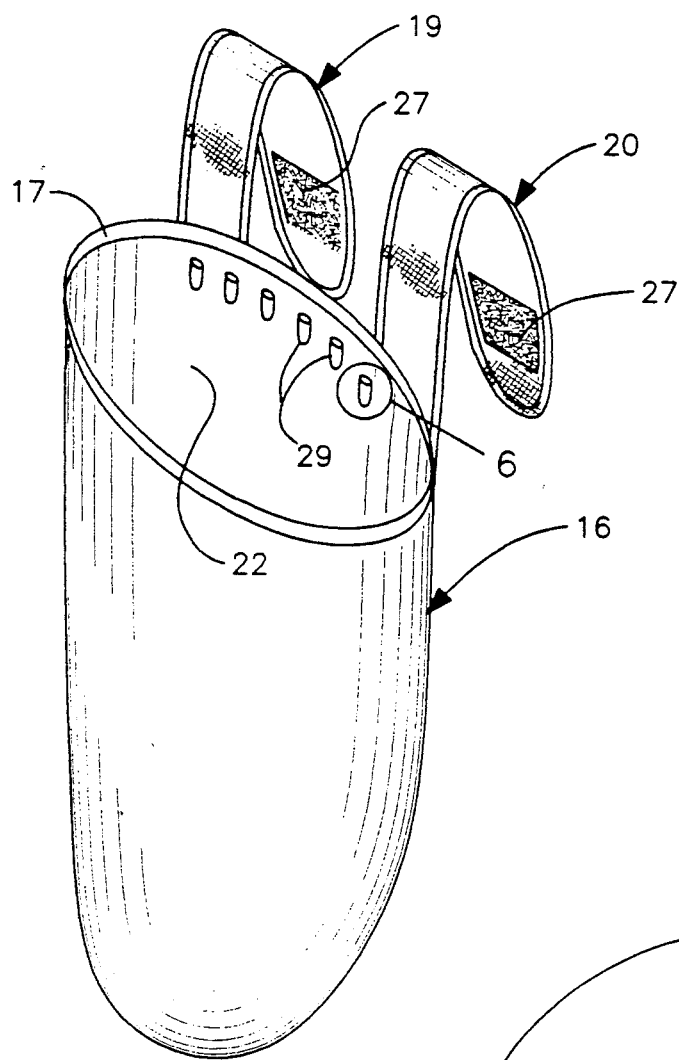
FIG. 5 is an isometric illustration of the sock structure employing lubricant tubes therewithin.
Figure 6:
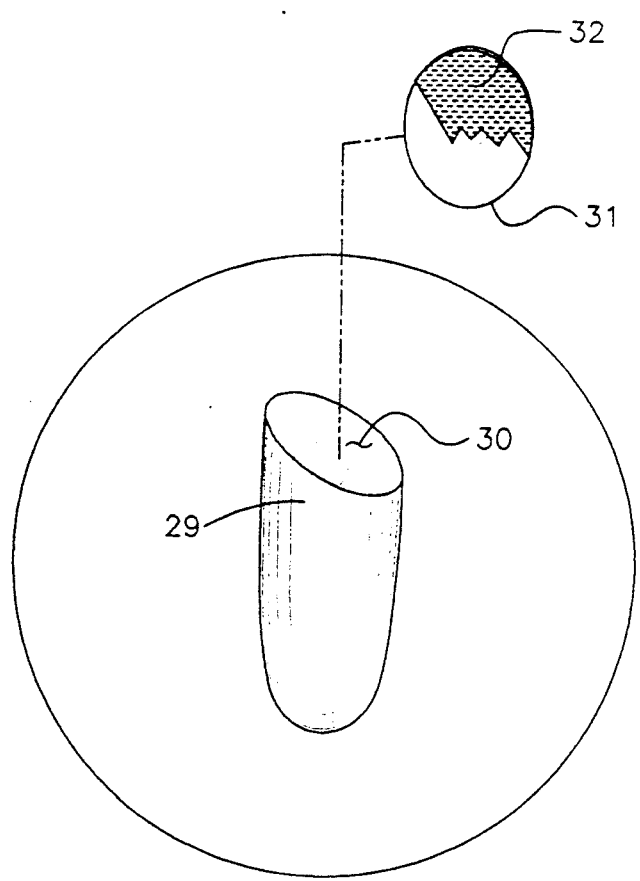
FIG. 6 is an enlarged isometric view of section 6 as set forth in FIG. 5.

The FIG. 5 indicates the organization to include a row of porous flexible tube members 29 mounted to the sock interior surface 22 adjacent the periphery 17. Each of the tube members 29 is arranged to receive a frangible capsule 31 therewithin, as indicated in FIG. 6, having a lotion fluid 32 therewithin of any desirable skin lotion as commercially available, whereupon projection of an individual's leg portion within the sock structure, and more particularly within the sock interior surface 21, effects rupturing of the frangible capsule 31 for permitting seepage of the fluid lotion 32 through the tube members 29 to provide for soothing and healing of an individual's limb when positioned within the sock structure for extended periods of time.

Figure 7:
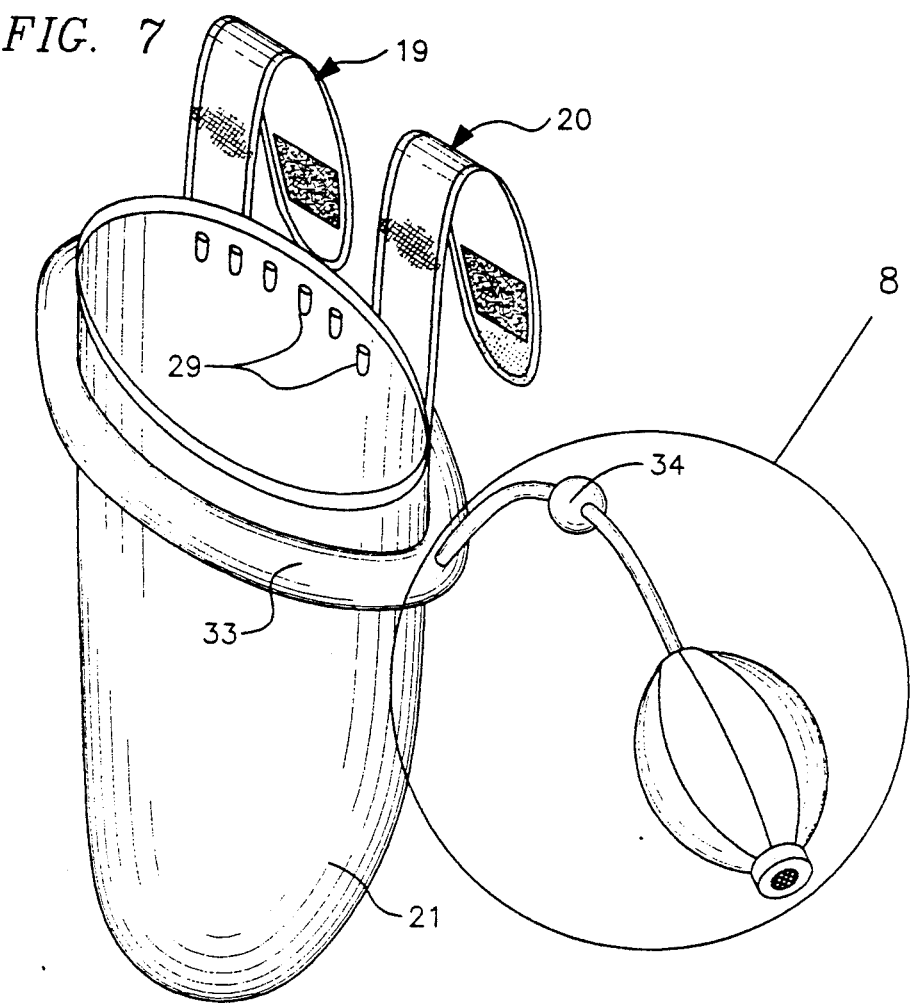
FIG. 7 is an isometric illustration of a further modified aspect of the invention.
Figure 8:
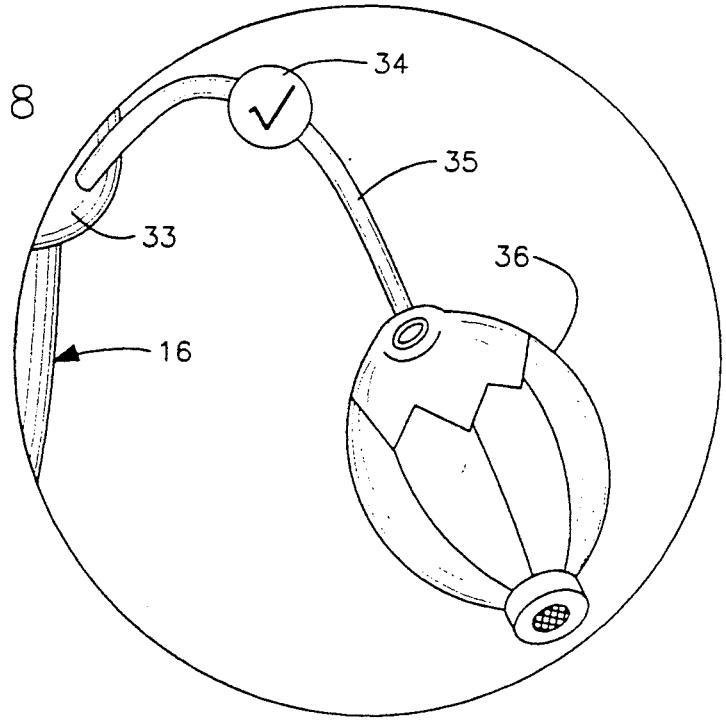
FIG. 8 is an isometric view, partially in section, of the inflation structure as indicated in FIG. 7.

The FIGS. 7 and 8 indicates the use of an optional pneumatic bladder 33 of a desired length, arranged in surrounding relationship relative to the sock exterior surface 21, having a pneumatic conduit 35 directed into the pneumatic bladder 33, including a check valve 34, with a pneumatic fill pump 36 arranged for directing pneumatic pressure through the conduit into the pneumatic bladder 33 for selective filling of the pneumatic bladder 33. In this manner, additional cushioning of an individual's limb portion when positioned within the sock body 16 is effected, as well as additional filling of the pneumatic bladder for assisting in filling of spacing of the exterior surface of the sock relative to the limb cavity surface.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A stump sock arrangement for use with an artificial limb, wherein the artificial limb includes a limb cavity, and wherein the stump sock arrangement comprises, a support strap, the support strap including a thigh strap, the thigh strap having an anchor strap fixedly and orthogonally mounted to the thigh strap, with the anchor strap arranged for securement to the artificial limb in adjacency to the limb cavity, and a flexible sock body, the flexible sock body having an exterior surface and an interior surface, and the interior surface including a body cavity, and the sock body having an entrance periphery for access to the body cavity, and a first strap and a second strap, each having a predetermined length, and each fixedly mounted to the entrance periphery in adjacency relative to one another in a coextensive relationship, wherein the first strap and the second strap are arranged for securement to the thigh strap, and the first and second straps are secured to the sock body at the entrance periphery, and the first strap and the second strap each include a strap outer surface directed in alignment with the sock exterior surface and the first strap and the second strap each having an inner surface in alignment and extending into the sock interior surface, wherein the interior surface of the first strap and the second strap each include a first hook and loop fastener patch spaced from a second hook and loop fastener patch, wherein each first hook and loop fastener patch is arranged for securement to a second hook and loop fastener patch for securement about the thigh strap, and an array of porous flexible tube members mounted within the sock cavity onto the sock interior surface in adjacency to the periphery, wherein each of the tube members includes a frangible capsule, wherein each frangible capsule includes a fluid contained therewithin for seepage onto an individual's leg portion directed into the flexible sock body.

2. A stump sock arrangement as set forth in claim 1 including a pneumatic bladder mounted about the flexible sock body secured to the sock exterior surface, with the pneumatic bladder including a pneumatic conduit directed into the pneumatic bladder, and a pneumatic pump, wherein the conduit includes a check valve directing one-way inflation of the pneumatic bladder from the pneumatic pump.

* * * * *